US010335039B2

(12) United States Patent
Xu

(10) Patent No.: US 10,335,039 B2
(45) Date of Patent: *Jul. 2, 2019

(54) METHODS FOR STENT STRUT DETECTION AND RELATED MEASUREMENT AND DISPLAY USING OPTICAL COHERENCE TOMOGRAPHY

(71) Applicant: LightLab Imaging, Inc., Westford, MA (US)

(72) Inventor: Chenyang Xu, Medford, MA (US)

(73) Assignee: LIGHTLAB IMAGING, INC., Westford, MA (US)

(*) Notice: Subject to any disclaimer, the term of this patent is extended or adjusted under 35 U.S.C. 154(b) by 190 days.

This patent is subject to a terminal disclaimer.

(21) Appl. No.: 15/288,199

(22) Filed: Oct. 7, 2016

(65) Prior Publication Data
US 2017/0020392 A1 Jan. 26, 2017

Related U.S. Application Data

(63) Continuation of application No. 13/907,217, filed on May 31, 2013, now Pat. No. 9,462,950, which is a
(Continued)

(51) Int. Cl.
A61B 5/00 (2006.01)
G06T 7/73 (2017.01)
(Continued)

(52) U.S. Cl.
CPC .......... A61B 5/0066 (2013.01); A61B 5/0084 (2013.01); A61B 5/6852 (2013.01);
(Continued)

(58) Field of Classification Search
CPC ... A61B 5/0066; A61B 5/0084; A61B 5/7425; A61B 5/6852; A61B 2576/00;
(Continued)

(56) References Cited

U.S. PATENT DOCUMENTS 5,054,492 A 10/1991 Scribner et al.
5,321,501 A 6/1994 Swanson et al.
(Continued)

FOREIGN PATENT DOCUMENTS

WO 2006076409 7/2006
WO 2007002685 1/2007

OTHER PUBLICATIONS

Bonnema et al., "An automatic algorithm for detecting stent endothelialization from volumetric optical coherence tomography datasets", Physics in Medicine and Biology, 53 :12, Jun. 21, 2008, pp. 3083-3098.
(Continued)

Primary Examiner — Joel Lamprecht
(74) Attorney, Agent, or Firm — K&L Gates LLP

(57) ABSTRACT

In one embodiment, the invention relates to a processor based method for generating positional and other information relating to a stent in the lumen of a vessel using a computer. The method includes the steps of generating an optical coherence image data set in response to an OCT scan of a sample containing at least one stent; and identifying at least one one-dimensional local cue in the image data set relating to the position of the stent.

21 Claims, 24 Drawing Sheets

Related U.S. Application Data continuation of application No. 12/579,333, filed on Oct. 14, 2009, now Pat. No. 8,478,387.

(60) Provisional application No. 61/105,290, filed on Oct. 14, 2008.

(51) Int. Cl.

| | | |
|---|---|---|
| *G06K 9/46* | (2006.01) | |
| *G06K 9/62* | (2006.01) | |
| *G06T 5/00* | (2006.01) | |
| *G06T 7/00* | (2017.01) | |
| *G06T 7/11* | (2017.01) | |
| *G06T 7/246* | (2017.01) | |
| *G06T 7/90* | (2017.01) | |

(52) U.S. Cl.
CPC .............. *A61B 5/7425* (2013.01); *G06K 9/46* (2013.01); *G06K 9/6267* (2013.01); *G06T 5/00* (2013.01); *G06T 7/0012* (2013.01); *G06T 7/11* (2017.01); *G06T 7/246* (2017.01); *G06T 7/73* (2017.01); *G06T 7/90* (2017.01); *A61B 2576/00* (2013.01); *G06K 2009/4666* (2013.01); *G06T 2207/10101* (2013.01); *G06T 2207/20061* (2013.01); *G06T 2207/20182* (2013.01); *G06T 2207/30101* (2013.01)

(58) Field of Classification Search
CPC ... G06T 7/90; G06T 7/11; G06T 7/246; G06T 5/00; G06T 7/0012; G06T 7/73; G06T 2207/20182; G06K 9/46; G06K 9/6267; G06K 2009/4666
See application file for complete search history.

(56) References Cited

U.S. PATENT DOCUMENTS

| | | |
|---|---|---|
| 5,459,570 A | 10/1995 | Swanson |
| 5,465,147 A | 11/1995 | Swanson |
| 5,488,674 A | 1/1996 | Burt et al. |
| 5,509,093 A | 4/1996 | Miller et al. |
| 5,531,227 A | 7/1996 | Schneider |
| 5,662,109 A | 9/1997 | Hutson |
| 5,748,598 A | 5/1998 | Swanson et al. |
| 5,771,895 A | 6/1998 | Stager |
| 5,784,352 A | 7/1998 | Swanson et al. |
| 5,797,849 A | 8/1998 | Vesely et al. |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,208,883 B1 | 3/2001 | Holupka et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,879,851 B2 | 4/2005 | McNamara et al. |
| 6,891,984 B2 | 5/2005 | Petersen et al. |
| 7,208,333 B2 | 4/2007 | Flanders et al. |
| 7,241,286 B2 | 7/2007 | Atlas |
| 7,397,935 B2 | 7/2008 | Kimmel et al. |
| 7,414,779 B2 | 8/2008 | Huber et al. |
| 7,415,049 B2 | 8/2008 | Flanders et al. |
| 7,593,559 B2 | 9/2009 | Toth et al. |
| 7,729,746 B2 | 6/2010 | Redel et al. |
| 8,298,147 B2 | 10/2012 | Huennekens et al. |
| 8,478,387 B2 | 7/2013 | Xu |
| 8,983,580 B2 | 3/2015 | Boppart et al. |
| 9,622,706 B2 * | 4/2017 | Dick .................... A61B 5/0062 |
| 2002/0115931 A1 | 8/2002 | Strauss et al. |
| 2005/0201662 A1 | 9/2005 | Petersen et al. |
| 2005/0238067 A1 | 10/2005 | Choi |
| 2006/0095065 A1 | 5/2006 | Tanimura et al. |
| 2006/0165270 A1 | 7/2006 | Borgert et al. |
| 2006/0187537 A1 | 8/2006 | Huber et al. |
| 2006/0203859 A1 | 9/2006 | Cable et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2007/0115481 A1 | 5/2007 | Toth et al. |
| 2007/0123771 A1 | 5/2007 | Redel et al. |
| 2007/0167710 A1 | 7/2007 | Unal et al. |
| 2007/0260198 A1 | 11/2007 | Atlas |
| 2008/0100612 A1 | 5/2008 | Dastmalchi et al. |
| 2008/0161696 A1 | 7/2008 | Schmitt et al. |
| 2008/0165366 A1 | 7/2008 | Schmitt et al. |

OTHER PUBLICATIONS

Unal et al., "Stent implant follow-up in intravascular optical coherence tomography images," Int J Cardiovasc Imaging, DOI 10.1007/s10554-009-9508-4, published online Sep. 24, 2009, 8 pgs.

Xu et al., "Characterization of atherosclerosis plaques by measuring both backscattering and attenuation coefficients in optical coherence tomography," Journal of Biomedical Optics, 13:3, May/Jun. 2008, 8 pgs.

Takano et al., "Evaluation by Optical Coherence Tomography of Neointimal Coverage of Sirolimus-Eluting Stent Three Months After Implantation," American Journal of Cardiology, vol. 99, No. 8, Apr. 14, 2007, pp. 1033-1038.

International Search Report for International Application No. PCT/US2009/060714, dated Jan. 4, 2010, 6 pgs.

Written Opinion of the International Searching Authority for International Application No. PCT/US2009/060714, dated Jan. 4, 2010, 6 pgs.

English translation of Office Action of Japanese Patent Office dated Feb. 25, 2014 (6 pgs.).

* cited by examiner

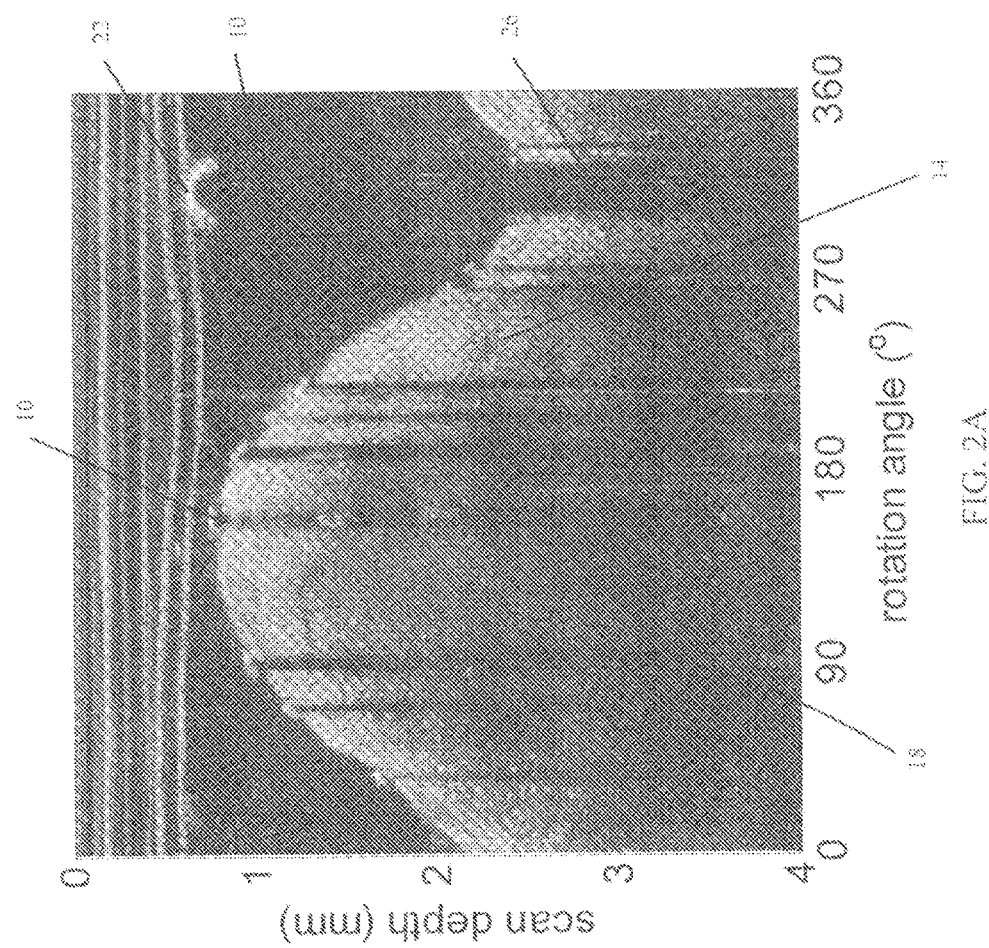

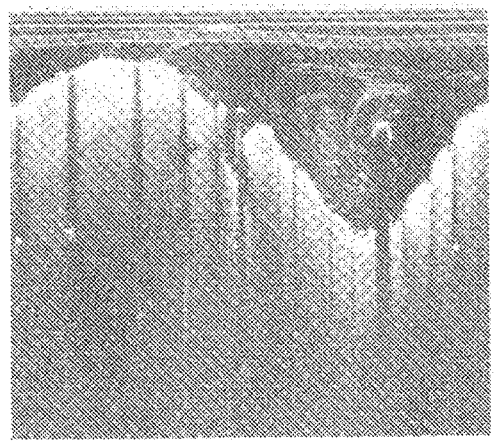
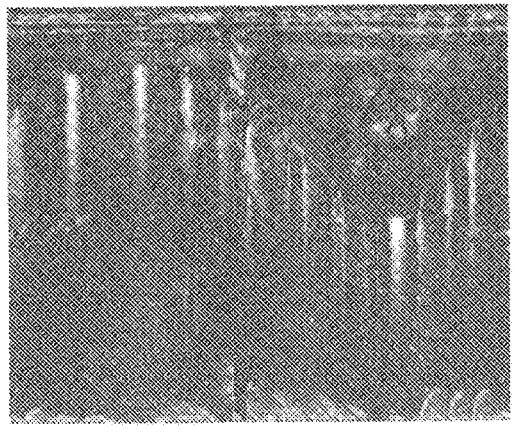
FIG. 7A  FIG. 7B
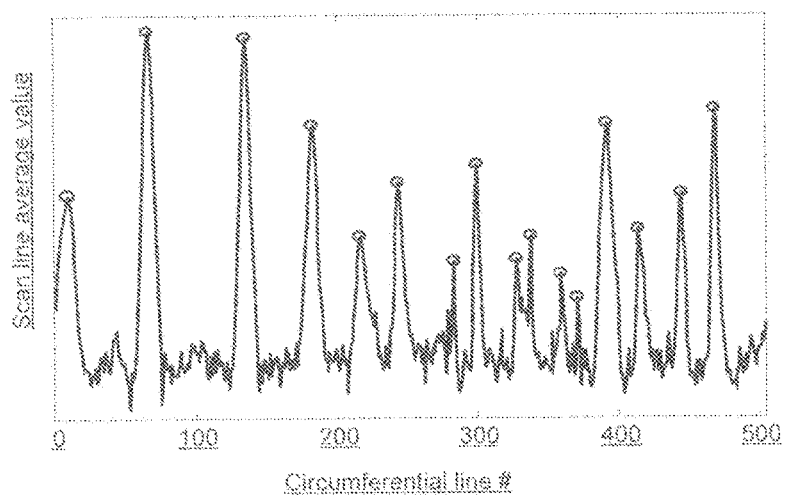
FIG. 7C

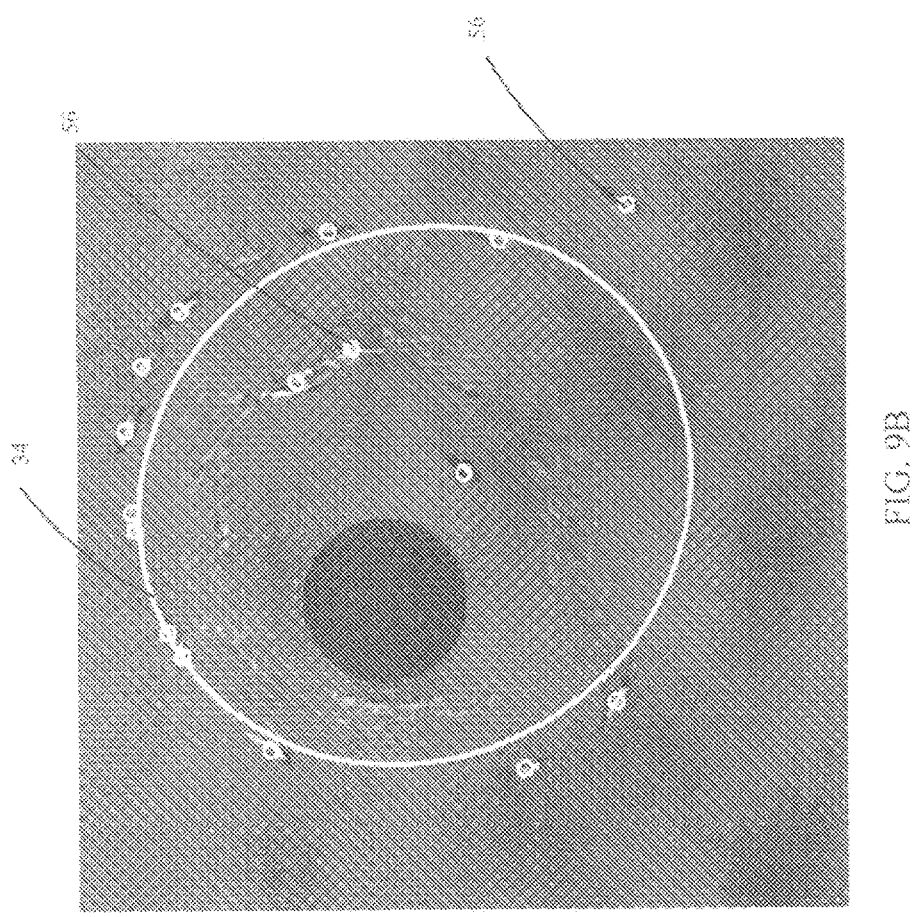

METHODS FOR STENT STRUT DETECTION AND RELATED MEASUREMENT AND DISPLAY USING OPTICAL COHERENCE TOMOGRAPHY

CROSS REFERENCE TO RELATED APPLICATIONS

This application is a continuation of U.S. patent application Ser. No. 13/907,217, filed on May 31, 2013 which is a continuation of U.S. patent application Ser. No. 12/579,333, filed on Oct. 14, 2009, now issued U.S. Pat. No. 8,478,387 which claims the benefit of priority under 35 U.S.C. § 119(e) to U.S. Provisional Application No. 61/105,290, filed Oct. 14, 2008, the entire disclosures of which are hereby incorporated herein by reference for all purposes.

FIELD OF INVENTION

This invention provides methods for automatic stent or stent strut detection and measurement using optical coherence tomography data, such as image data.

BACKGROUND

Optical coherence tomography (OCT) is an interferometric imaging technique with widespread applications in ophthalmology, cardiology, gastroenterology and other fields of medicine. The ability to view subsurface structures with high resolution (2-15 µm) through small-diameter fiber-optic probes makes OCT especially useful for minimally invasive imaging of internal tissues and organs. The latest generation of OCT systems can generate OCT images up to 100 frames per second, making it possible to image coronary arteries in the beating heart artery within a few seconds. OCT can be implemented in both the time domain (TD-OCT) and the frequency domain (Fourier domain OCT or optical frequency domain imaging, OFDI).

OCT imaging of portions of a patient's body provides useful tool for doctors to determine the best type and course of treatment. For example, imaging of coronary arteries by intravascular OCT may reveal the location of a narrowing or stenosis, the presence of vulnerable plaques, and the type of atherosclerotic plaque. This information helps cardiologists to choose which treatment would best serve the patient— drug therapy (e.g., cholesterol-lowering medication), a catheter-based therapy like angioplastry and stenting, or an invasive surgical procedure like coronary bypass surgery. In addition to its applications in clinical medicine, OCT is also very useful for drug development in animal and clinical trials.

A stent is a tube-like structure that can be inserted into a vessel to expand the vessel to counteract a stenotic condition that constricts blood flow. Stents typically are made of a metal or a polymer scaffold that can be deployed to the site of a stenosis via a catheter. During percutaneous transluminal coronary angioplasty (PTCA), a factory-installed stent is usually delivered to the stenotic site through a catheter via a guide wire, and expanded using a balloon to a preset pressure to enlarge the lumen of a stenosed vessel. The first stents employed in cardiovascular medicine were made of metal without a coating, i.e., bare-metal stents (BMS). Later, to reduce the probability of restenosis, drug-eluting stents (DES) were developed on which a polymer coating containing a growth-inhibiting drug was added.

There are several factors that influence the patient outcome of deploying stents during a PTCA procedure. During PTCA, the stents should be expanded to the right diameter that corresponds to that of adjacent healthy vessel segments. Stent overexpansion may cause extensive damage to the vessel, making it prone to dissection, disarticulation, and intra-mural hemorrhage. Stent under expansion may inadequately expand the vessel to restore normal flow. If the stent struts fail to contact the vessel wall (a condition called stent malapposition), the risk of thrombosis may increase. After PTCA and stenting, the stent surface usually will be covered by a layer of endothelial cells as a result of a process called re-endothelization. Re-endothelization may be interrupted by diseases or drugs such as those used in DES. Although anticoagulant drugs are frequently prescribed for a period of 6 months to one year after the implantation of a stent, there is a the risk of a late-thrombotic event if administration of the drugs is stopped before the stent components or struts are re-endothelized completely. On the other hand, the inflammatory response of the vessel to the stent may induce excessive tissue proliferation and restenosis, possibly narrowing and closing the newly opened vessel.

SUMMARY OF THE INVENTION

OCT is suited for imaging stents, because it provides high resolution (5-20 µm) of thin tissue layers and high contrast between the stent struts and neighboring tissues. The quantitative measurement of deployed stent diameter, malapposition during PTCA, degree of endothelial stent coverage, and restenosis during follow-up are important parameters for cardiologists to make clinical decisions. However, to measure these parameters with OCT, it is cumbersome and time-consuming for human operators to mark the stent struts and lumen boundary individually.

To facilitate stent visualization and measurement, it is important to develop semi-automatic and automatic methods for stent strut detection and lumen boundary detection. The appearance of stents may be influenced by the stent type, the thickness and composition of the tissue layers on top of the stents, and the OCT imaging conditions. Therefore, different detection methods may be required for different OCT images. Different detection methods should also be tuned for different OCT imaging goals (e.g., for freshly implanted stents, the goal may be malapposition; while for following up imaging of drug-eluting stent, the goal may be measurement of neointimal coverage).

Various imaging artifacts may also confound the detection of stent struts. For example, the geometrical accuracy along the lateral direction may be affected by NURD (non-uniform rotation distortion), resulting in a stretched or compressed appearance of the lateral dimension of the struts. The geometrical accuracy along the pullback direction may also be affected by non-uniform relative pullback speed between the imaging element and the tissue being imaged. For best visualization and measurement, these artifacts need to be detected and corrected.

Accordingly, it is highly desirable to have reliable efficient methods for detection of stent struts and stents for visualization and measurement. Preferably, the methods should also be able to tolerate or correct for various imaging artifacts.

The present invention relates to an apparatus and methods for computer-assisted detection of a stent, a stent strut, or other stent portion or component for measurement and characterization of malapposition, neointima growth and restenosis in OCT images. Methods are disclosed for circumscribing the lumen boundary and for localizing the stent struts. In one embodiment, struts are detected on the basis of their shadowing properties in a 2-D image. In a second embodiment, the stent struts are detected by using the elongated appearance of the struts in OCT images. In a third embodiment, because some stents are composed of wire meshes that are continuous in 3-D, the 3-D cues are used to detect struts and refine struts detection. In a fourth embodiment, various stent distortion types or related artifacts are corrected.

Certain aspects provide a method for generating positional and other information about a stent in the lumen of a vessel using a computer. The method can include the steps of: generating an optical coherence image data set in response to an OCT scan of a sample containing at least one stent; and identifying at least one one-dimensional local cue in the image data set relating to the position of the stent.

In some embodiments, the one dimensional local cue is an intensity profile of the optical coherence image data set. In some embodiments, the one dimensional local cue is a shadow profile in the optical coherence image data set. In some embodiments, the one dimensional local cue is a strut line-like shape in the optical coherence image data set. In some embodiments, the method can include the step of determining the lumen boundary in the optical coherence image data set.

In some embodiments, the one dimensional local cue is a shadow profile in the optical coherence image data set and the method can include the steps of: defining a depth below the lumen boundary in the optical coherence image data set; and determining the average intensity of each vertical scan in the optical coherence image data set between the lumen boundary and the depth below the lumen boundary in the image data set to form an intensity profile for the optical coherence image data set. In some embodiments, the method can include determining the shadow profile using an edge detector.

In some embodiments, the method can include determining the shadow profile using a ridge detector. In some embodiments, the method can include determining the strut line-like shape is determined using a ridge detector. In some embodiments, the method can include identifying two dimensional local cues in the optical coherence image data set. In some embodiments, a two dimensional local cue is calculating a curve fit of detected stent points to an ellipsoidal distribution.

In some embodiments, the method can include the step of removing detected stent points that do not fit on the ellipsoidal distribution. In some embodiments, the method can include the steps of: identifying at least one three dimensional local cue in the image data set; and generating a modified image data set using the at least one three dimensional local cue. In some embodiments, the method can include the step of using line detector to detect 3-D struts.

Certain aspects provide a method for measuring stent position in the lumen of a vessel. The method can include the steps of: measuring a distance from a detected stent portion to a lumen edge; and calculating one or more of stent malapposition, neointima coverage, or restenosis data in response to the distance from the detected stent position to the lumen edge.

Certain aspects provide a method for displaying stent related measurement data generated from an OCT image data set. The method can include the steps of: collecting OCT data with respect to a location of a stent in the lumen of a vessel; analyzing the OCT data to generate an image data set relating to an image of a stent; displaying the image data set as in a two dimensional surface map, and overlying measurements on the displayed surface map using symbols.

Certain aspects provide a method for motion artifact removal in collected OCT image datasets. The method can include the steps of: examining an OCT image data set to locate aperiodicity of strut image data in the image data set; and applying a function to restore periodicity of strut image data in the image data set.

In some embodiments, the method can include the steps of: using angiography during OCT image data collection; determining the relative speed of OCT catheter movement within the lumen in which the catheter is disposed; and storing the periodicity of the strut image data in response to catheter speed.

Certain aspects provide a system for generating positional and other information about a stent in the lumen of a vessel. The computer system can include an electronic memory device and an electronic processor in communication with the memory device. The memory device can include instructions that when executed by the processor cause the processor to generate an optical coherence image data set in response to an OCT scan of a sample containing at least one stent and identify a plurality of local cues in the image data set relating to the position of the stent.

In some embodiments, at least one of the plurality of local cues is selected from the group consisting of a one-dimensional cue, a two-dimensional cue, a three-dimensional cue, an intensity profile, a shadow profile, a strut line-like shape, a ridge, a edge, and a valley.

BRIEF DESCRIPTION OF THE DRAWINGS

The objects and features of the invention can be better understood with reference to the drawings described below. The drawings are not necessarily to drawn to scale; emphasis is placed instead being placed on illustrating the principles of the invention. In the drawings, numerals are used to indicate specific parts throughout the various views. The drawings associated with the disclosure are addressed on an individual basis within the disclosure as they are introduced.

FIGS. 7 (A, B and C) illustrate an example of shadow formation adjacent stent struts, shadow detection using adaptive ridge (valley) detection, and a graphical representation of the intensity of the ridges, respectively;

DETAILED DESCRIPTION

The following description refers to the accompanying drawings that illustrate certain embodiments of the invention. Other embodiments are possible and modifications may be made to the embodiments without departing from the spirit and scope of the invention. Therefore, the following detailed description is not meant to limit the invention. Rather, the scope of the invention is defined by the appended claims.

In general, the invention relates to an apparatus and methods for stent detection and related measurement/visualization problems based on images obtained using optical methods based on optical coherence interferometry, such as low coherence interferometry (LCI), and further including, but not limited to, optical coherence domain reflectometry, optical coherence tomography (OCT), coherence scanning microscopy, optical coherence domain imaging (OFDI) and interferometric microscopy.

In one embodiment relating to stent detection, a sequence of samples along a ray originating at the catheter center to the maximum imaging depth is referred to as a scan line. An OCT image is typically acquired one scan line at a time. Thus, a given scan line can correspond to a one-dimensional cue or indicia of a stent strut or stent portion. A cross-sectional image is formed by a collection of scan lines as the catheter rotates. Given the high reflectivity of various stent materials and other parameters, stents and OCT image data that are correlated with stents can be identified as a cue or other indicia corresponding to a stent. Further, to image a segment of the vessel, the catheter is moved longitudinally while rotating, hence acquiring a set of cross-sectional images in a spiral pattern. Thus, a three-dimensional profile of a stent relative to a lumen boundary can be detected and displayed.

It should be noted that while the present invention is described in the context of OCT images, the present invention is not so limited. Thus, for example, identifying any stent, stent portion, strut, or any edge, valley, ridge, region of high reflective correlated or associated with a stent in any vascular image or related OCT data set is within the spirit and scope of the present invention.

Figure 1:
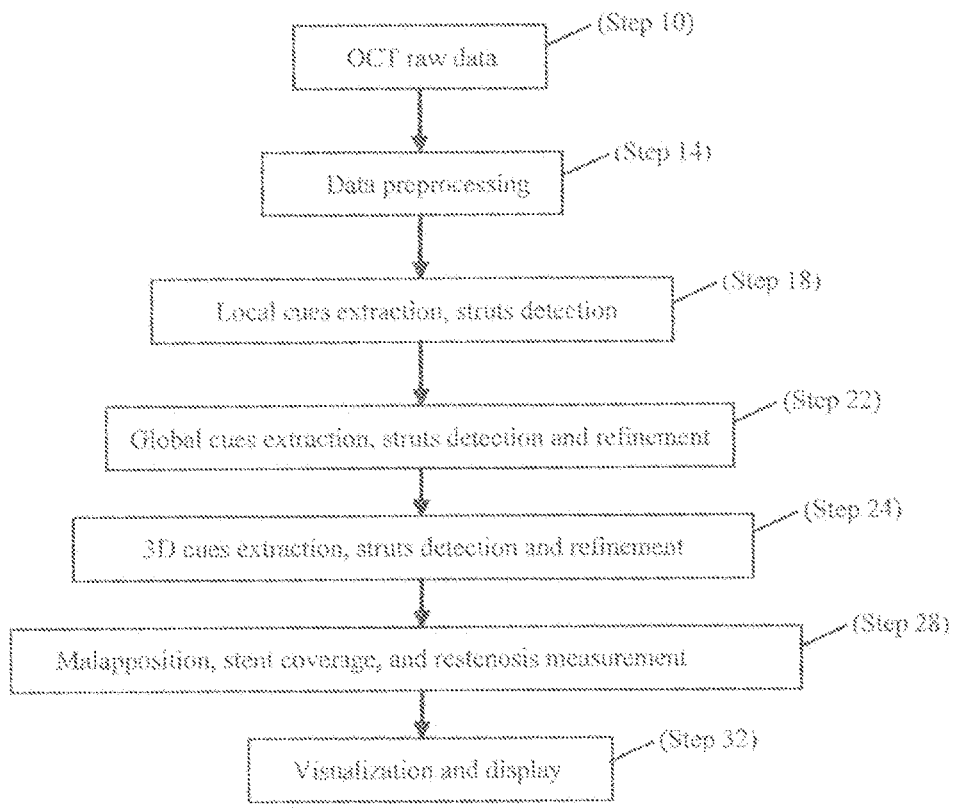
FIG. 1 illustrates a flow chart representing an embodiment of a method practiced in accordance with the present invention for detecting stent struts.

For the automatic and non-automatic detection approaches described herein to function properly, there must be features detectable from the image that defines the object to be detected from background objects. In one embodiment of the invention, three levels of cues are used to detect the object from the background: local cues (a 1-D scan line or a additional neighboring scan lines, a one dimensional local cue), global cues (2-D image) and 3-D cues. An example of the steps utilizing these cues is shown in FIG. 1. The disclosed detection scheme works, in outline, as follows. An OCT image is obtained (Step 10) and after noise-removal and artifact correction (Step 14), the shadow effect and/or the ridge shape of the metal struts are used to localize the struts as described below (Step 18). After integrating all the local cues, the 2-D image cues are used for additional localization as well as localization and refinement of the detection (Step 22).

In one embodiment, the struts are localized within a ring described by an ellipsoidal function or model, with the ridge of the struts located within a boundary area defined by an ellipsoid. Finally, 3-D cues are used for further localization and refinement of the localization (Step 24). For example, according to one implementation, the struts are confined to lie within a continuous wire mesh that has a known 3-D structure. Once the stent location and the lumen boundary have been determined, stent malapposition, coverage and restenosis measurements are made (Step 28). Finally, the images and measurements are visualized and displayed (Step 32).

Figure 2B:
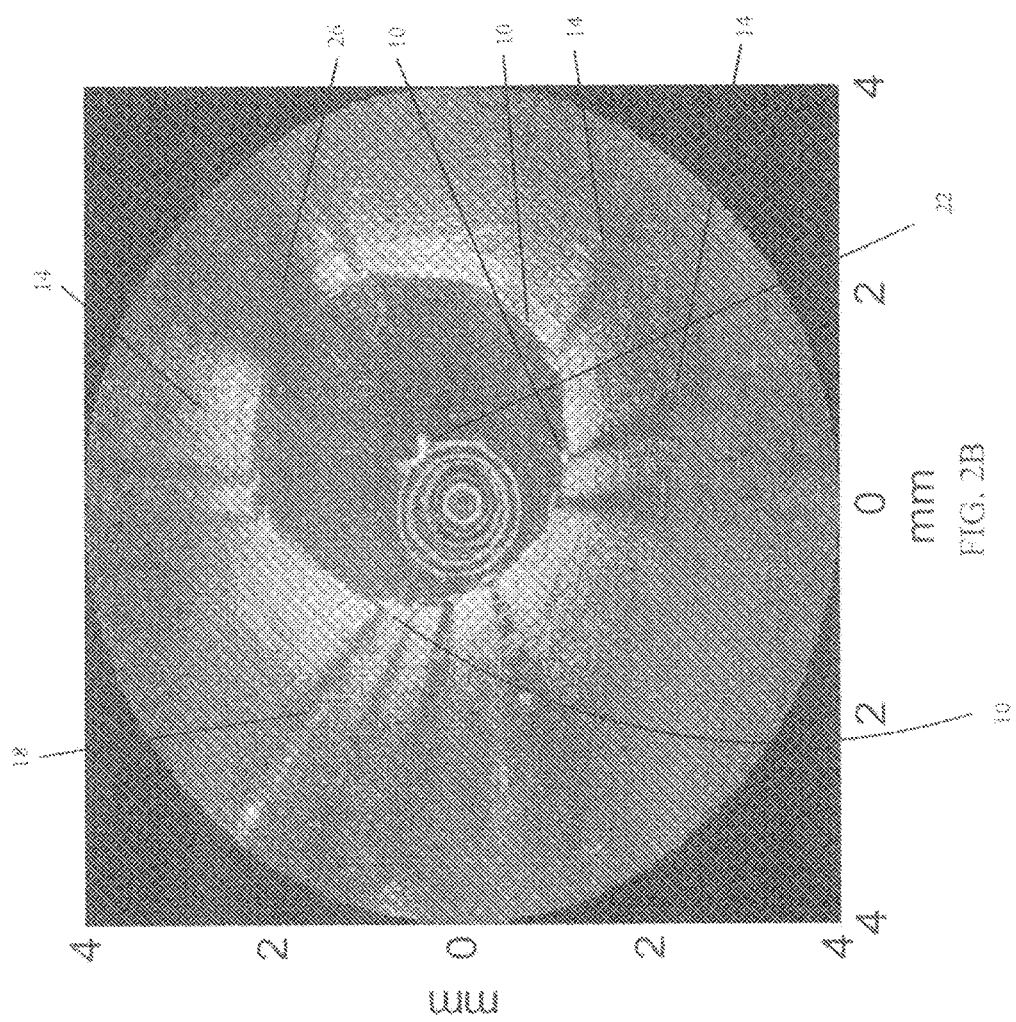
FIGS. 2 (A and B) illustrate an example of an OCT image of a recently implanted stent or stents with thin tissue coverage, before and after rectangular-to-polar conversion respectively.

Below is an explanation of steps employed in one embodiment of the present invention to localize stent struts according to local image cues. In FIG. 2A, the image shows a visualized example of the raw OCT image obtained from the OCT imaging device. The image in FIG. 2B shows the processed OCT image for displaying to the viewers after rectangular to polar conversion. In both images the stent struts appear as bright areas 10 indicating their high reflectivity to the incident OCT light beam. The high reflectivity of the stent substantially prevents the OCT light beam from penetrating into the lumen 14. This lack of beam penetration causes shadows 18. The guidewire 22 also casts a shadow 26. In one embodiment, it is possible to use various depths for different scan lines. For example, it is possible to calculate the intensity relative to the depth of the noise floor associated with OCT imaging noise in areas where no structure is present, such as a the lumen itself or other void regions. Further, it is possible to apply a threshold to the image to generate a binary image, then calculate the shadow based on that binary image. In some embodiments, using a black and white image (binary image) instead of a gray scale image offers certain image processing speed and accuracy enhancements.

Conversion to the polar view results in information loss that makes stent analysis more difficult. For stent detection, it is more accurate and convenient to start with the raw OCT image before the rectangular-to-polar conversion. Starting from the raw OCT image, the next steps in one embodiment are to perform lumen or lumen wall detection, to detect the angular position of the struts using image information, and to detect the depth of struts in the image scan lines.

Figure 3:
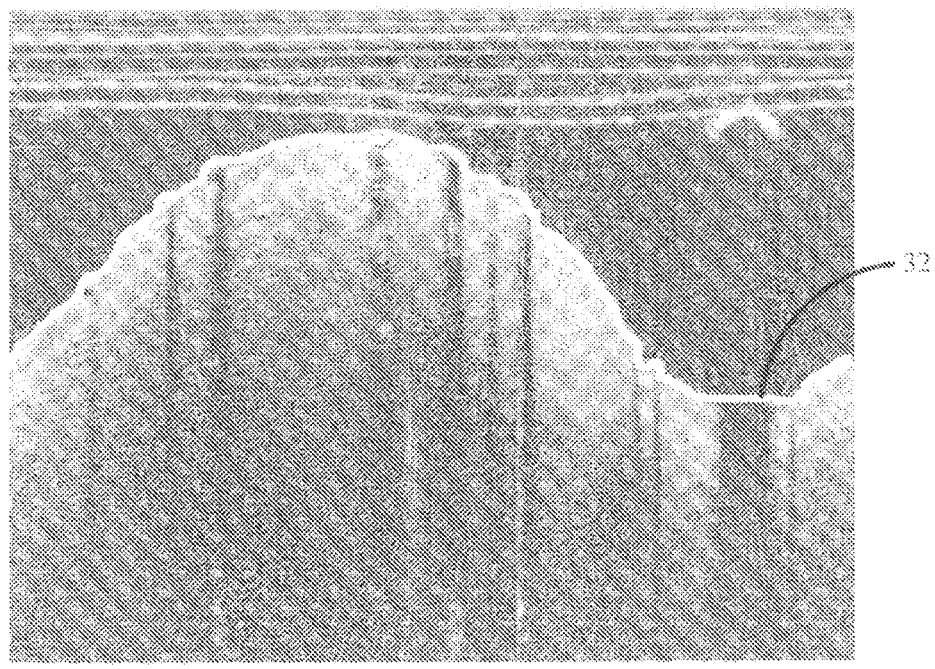
FIG. 3 illustrates an example of automatic lumen boundary detection.

Referring to FIG. 3, lumen or lumen boundary detection can be achieved by various image segmentation methods. In one embodiment, lumen detection is achieved by applying a threshold value to the smoothed image and determining a single lumen-tissue boundary that exhibits the best fit to the lumen data. The boundary 32 is chosen such that the boundary maximizes the area above the threshold while not encroaching into the area below the threshold.

In general, as discussed above stent struts in OCT images appear to be bright narrow features. Typically, these features are immediately followed by shadows. Therefore, the detection of struts and their localization can be achieved either by analyzing the associated low-signal shadows or by the bright narrow ridge-like features.

Figure 4:
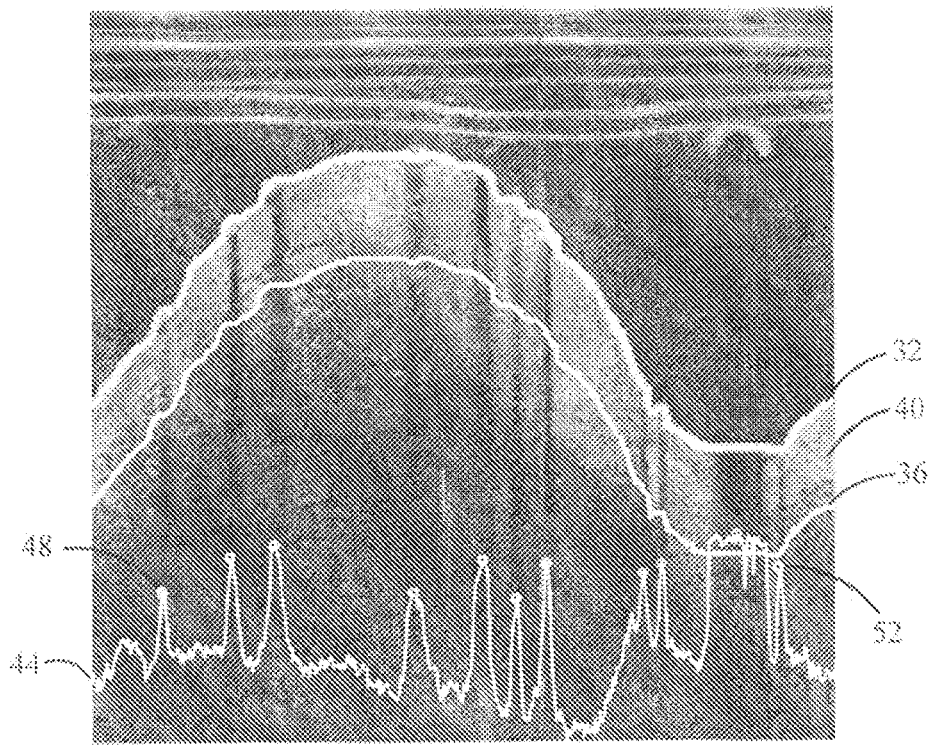
FIG. 4 illustrates an example of a region of a vessel wall chosen for shadow detection.
Figure 5:
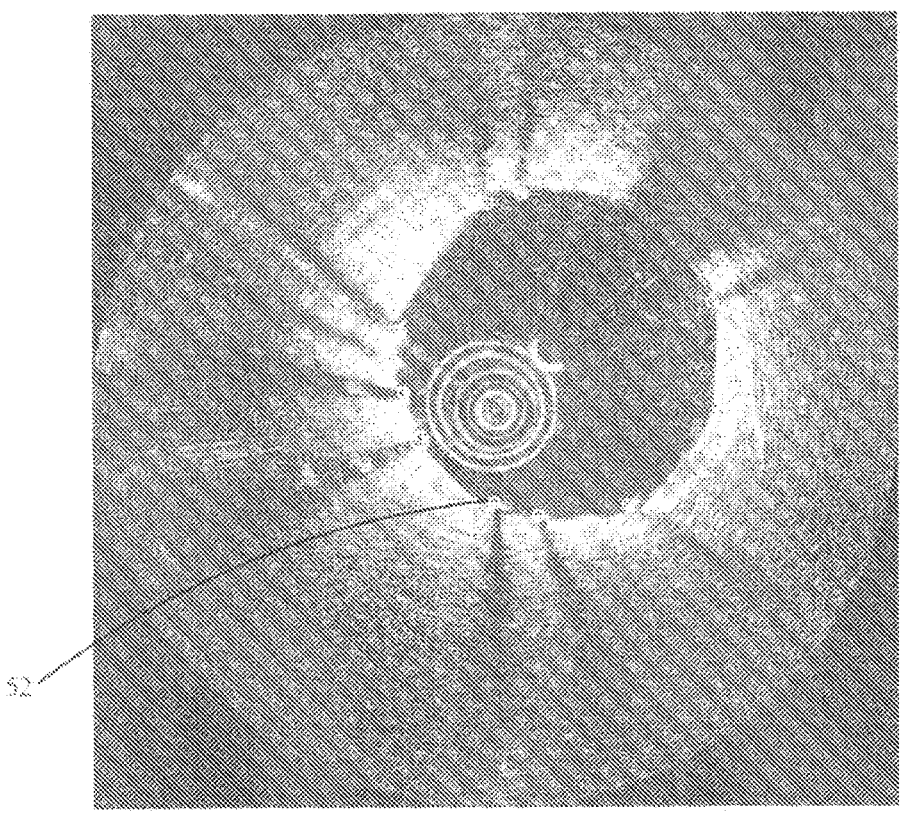
FIG. 5 illustrates an example of stent strut localization after rectangular to polar conversion.

In one embodiment, detecting the stent associated shadow is performed by interrogating the intensity profile of an image area below the lumen surface. For example, and referring to FIG. 4, by averaging the intensity within each scan line (vertical line) in the region 40 from lumen boundary 32 to a certain depth 36 (e.g., 500 μm,) or to the depth at which the OCT signal drops to certain pre-defined level 36, the struts can be detected as the horizontal position in the image where the graphed average intensity 44 (FIG. 4) of the vertical scan line is at a minimum 48. This follows because the shadows have much lower intensity than the surrounding tissue. Once the relative minima of the image intensity data are determined, the centers of such relative minima are used to estimate the position of the stent strut. In FIG. 5, these relative minima 52 are plotted on the boundary of the lumen image in polar coordinates to indicate the stent strut locations.

Figure 6:
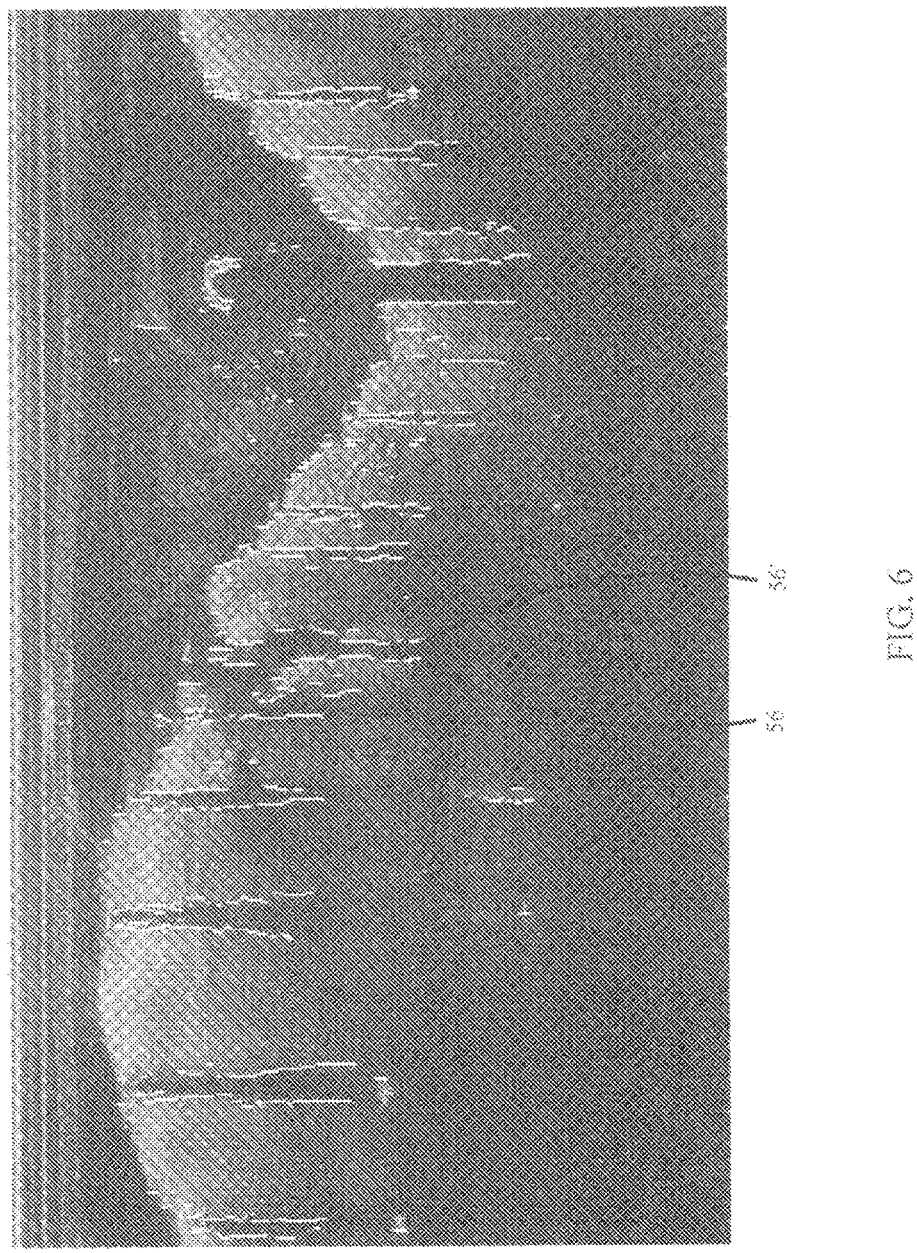
FIG. 6 illustrates an example of shadow formation adjacent stent struts and shadow detection using edge detectors.

Another way to detect the associated shadow is by using an edge detector. Because the stents are often made of light-blocking material such as metal, the shadow in the surrounding tissue has a sharp edge in which the transition length is approximately equal to the lateral resolution of the imaging system. Referring to FIG. 6, there are two sharp edges 56, 56' for each shadow corresponding to the edges of the stent struts. These edges may be detected using any suitable image processing tools such as edge or ridge detecting filters. Ideally, the edge detecting filters utilize the fact that the edges are all substantially vertical, i.e., the edge line is projected radially from the imaging probe.

Yet another way to detect the associated shadow is using a ridge (or valley detector depending upon orientation). Referring to FIG. 7A, a shadow can be viewed as the inverted ridge (valley) amid surrounding tissues because it is usually the local intensity minima and it is substantially vertically oriented. Because the width of shadow varies with the width of the struts, the scale of the ridge detector should be variable. Referring to FIG. 7, ridge-detecting filters are applied to the original image (FIG. 7A) to obtain the ridge intensity level map (FIG. 7B). The ridge intensity at each scan or horizontal location is averaged in the vertical direction to generate the ridge intensity profile image or map. The average intensities of this map are then graphed and the peaks in the graph are detected. The peaks correspond to the location of the centers of the stent struts. (FIG. 7C). The stent struts can also be detected directly by using its bright ridge-like features. This is especially useful when the strut shadows are diminished because the struts are buried deeply inside tissue, when the multiple scattering effect diminishes the contrast between the shadows and the surrounding tissue. As the incident light goes deeper into the tissue, the scattering effects increase which further diminishes the contrast.

Because the metal struts are highly reflective, the brightness of struts in an image is often high. For a bright point object, the size of that imaged point in OCT is not a point, but a smeared image point the size of the system resolution. Similarly, the size of a bright object in an OCT image is the sum of the size of the object itself and the resolution of the OCT system. For struts, in the axial (vertical) direction, the light is reflected from the top surface. Therefore, the size of struts in the axial direction is the OCT axial resolution, which is about 10-20 um. The lateral resolution is the sum of the actual struts width and the lateral resolution, which is much larger, ranging from 100-1000 um. Since the metal struts are opaque, the depth-spread of struts in image is approximated by the axial resolution of the OCT imaging system (which usually is around 10-20 μm). Conversely, the horizontal spread of struts is approximately equal to the sum of the struts width and the lateral resolution of the OCT imaging system. The horizontal spread is approximately 100-1000 μm, depending on the stent types and the OCT resolution at various depths.

Figure 8A:
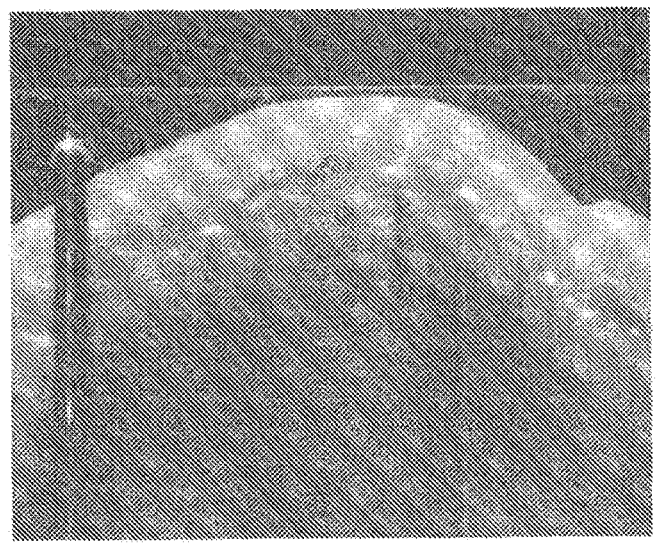
FIGS. 8 (A, B and C) illustrate an example of stent strut visualization, isolation and detection using a ridge detector.
Figure 8B:
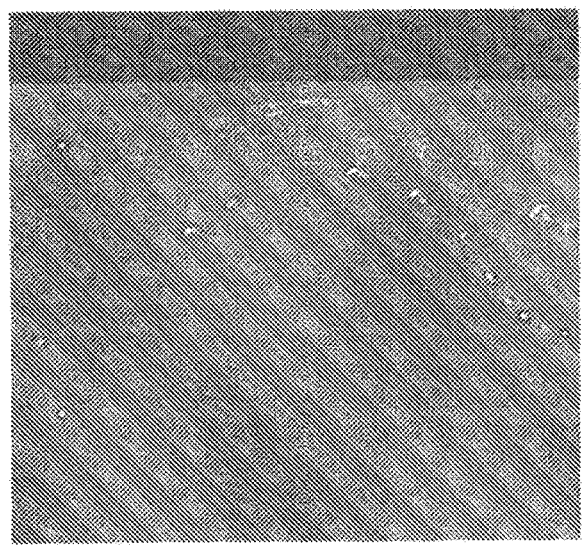
Figure 8C:
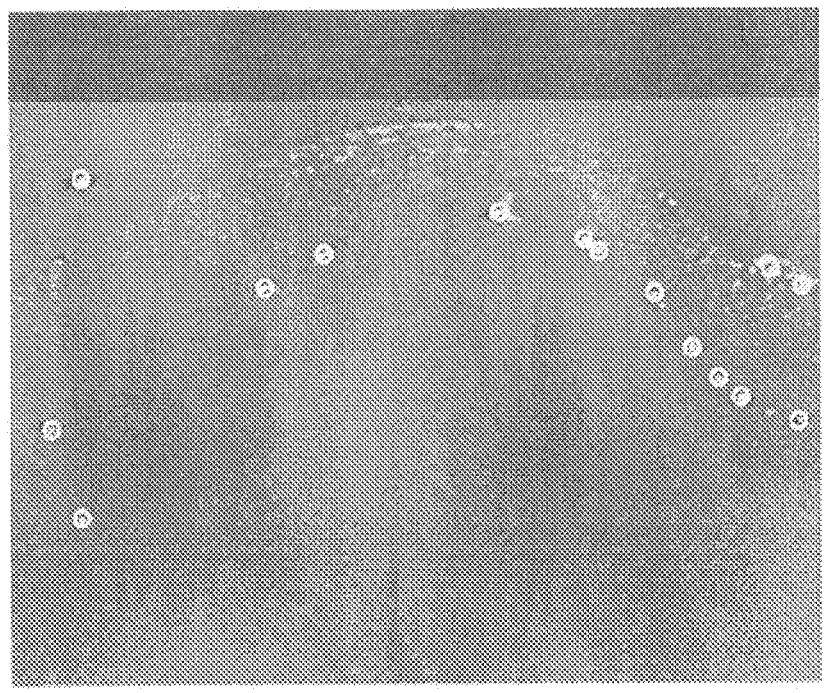

Therefore, each strut usually appears as bright elongated (or ridge-like) features. These elongated features can be detected using ridge detectors known in the image processing art. FIG. 8 shows an example of ridge detection using a Hessian matrix. The Hessian matrix is applied to the original image (FIG. 8A) to obtain the ridge intensity map (FIG. 8B). Then a threshold is applied and the centroids of the elongated features are used to determine the location of the centers of the stent struts (FIG. 8C).

Figure 9A:
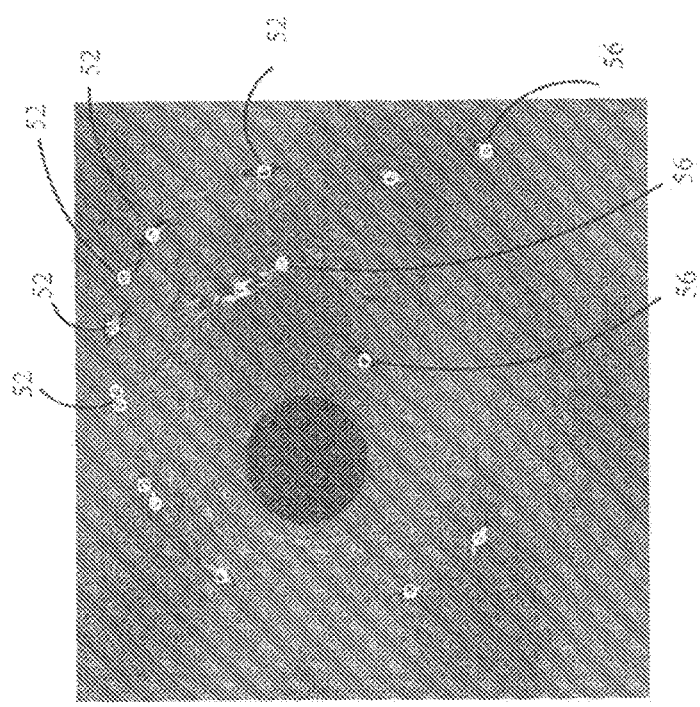
FIGS. 9 (A and B) illustrate an example lumen detection in which a threshold has bee applied to FIG. 8A and after fitting the relevant data to an ellipse, respectively.

Errors in the detection of struts based on local cues alone can occur if images of tissue structures produce "strut-like" features. The use of 2-D cues can reduce such misdetections. Take for example FIG. 9A, which is 8 C after rectangular-to-polar conversion. It is apparent that the stent struts 52 should be lying on an approximate ellipse while most of the out-of-ellipse detections 56 are misdetections caused by noise. An ellipsoid curve fitting method or other model-fitting method which fits the maximum number of points to an ellipse can be used to reject the misdetections, as shown in FIG. 9B. In most analyses of stents in a clinical or research setting, it is preferable to exclude stent struts with ambiguous images to avoid the possibility of introducing bias into statistical measurements. In addition to the refinement of strut detection based on local cues, the 2-D global cues can be used for detection itself. However, in other embodiments, methods can be used to detect 2-D stent features directly rather than by identifying points that fit an ellipsoid. For example, the Hough transform, can be used to detect the 2-D ellipse features from an image.

In addition because the stent is an extended cylindrical structure, information in a third dimension should be useable to define the locations of the struts relative to the vessel. That is, the struts in a 3-D OCT image should form continuous wire mesh. As with 2-D cues, 3-D cues can be used for both detection and refinement. To detect struts based on 3-D cues, a series of 2-D images are stacked to form a 3-D volume. The struts are then detected using 3-D line or ridge detection algorithms. One embodiment of a 3-D line detector utilizes a 3-D Hessian matrix. After a Hessian matrix is determined, the line strength is calculated by obtaining the eigen values of the Hessian matrix. A predefined threshold is then applied to the eigen values to obtain the resulting line.

The Hessian matrix for detecting 3-D lines is a standard method. As an exemplary description of the matrix and other line detection techniques, a suitable reference includes "Three-dimensional multi-scale line filter for segmentation and visualization of curvilinear structures in medical images", Sato Y, Nakajima S, Shiraga N, Atsumi H, Yoshida S, Koller T, Gerig G, and Kikinis R, Medical Image Analysis, Volume 2, Issue 2, June 1998, Pages 143-168.

Specific steps relating to one exemplary method that uses the Hessian matrix is recited below. In one example of line detection, the first step is to create the Hessian matrix of an image after it has been filtered by a Gaussian blurring kernel. An exemplary Hessian matrix is as follows.

$$H(\vec{x}) = \nabla^2 I(\vec{x}) = \begin{bmatrix} I_{xx}(\vec{x}) & I_{xy}(\vec{x}) & I_{xz}(\vec{x}) \\ I_{yx}(\vec{x}) & I_{yy}(\vec{x}) & I_{yz}(\vec{x}) \\ I_{zx}(\vec{x}) & I_{zy}(\vec{x}) & I_{zz}(\vec{x}) \end{bmatrix}$$

As shown above, the elements of the Hessian matrix are scalar intensities. As used in the Hessian matrix, the components of the Hessian matrix may be matrices themselves relating to one or more images.

In this context, a 3-D blurring kernel is the three dimensional analogy of a 1 dimensional or a two dimensional kernel. As an example, the step of convolving a 1-D array X with vector [1 1] is a type of 1-D averaging or smoothing. As is known in the image processing arts, a kernel can be used to smooth the underlying data prior to further analysis. Typically, in various embodiments the kernel is a longer vector, and in one embodiment the system and methods described herein use a Gaussian profile to make it smoother. The next step is to calculate the eigen values of the Hessian matrix.

In turn, the third step is to calculate one or a group of parameters that are some combination of the eigen values and weighting functions. From a practical standpoint, it is difficult to set a threshold jointly on the three eigen-values. For example, for one eigen value, the threshold is a value, for two it is an area, and for three values it is a 3-D volume. In general, it is easiest to work with the 1-D case with one value. To address this difficulty, it is possible to use some prior information to weight and combine the eigen values to generate one parameter that is a likely candidate to best represent the line strength. As a result, with this candidate, it is only necessary to set one threshold. Thus, the final step is to set a threshold for parameters that are some combination of the eigen values and weighting functions to obtain "line detection" or the detection of a local cue of interest.

Figure 10A:
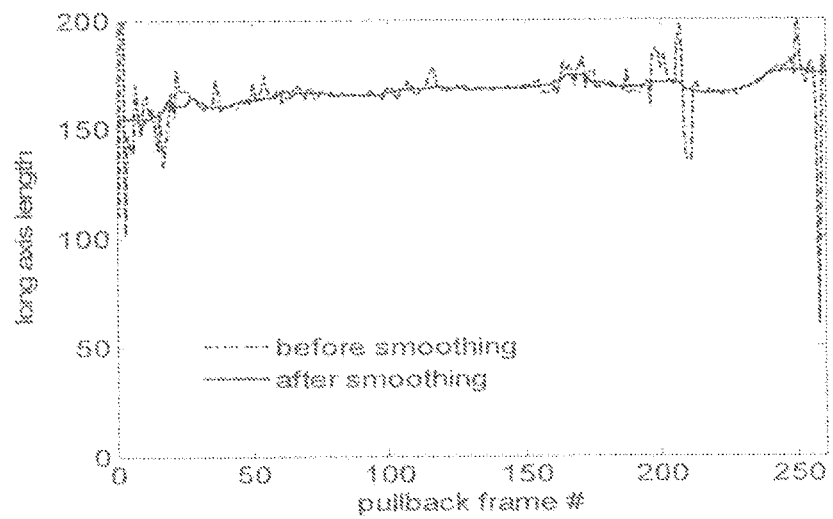
FIG. 10A is a graph which illustrates smoothing of long axis length measurement for different ellipses along pullback direction as an example of refining detection obtained from 2-D cues by 3-D cues.
Figure 10B:
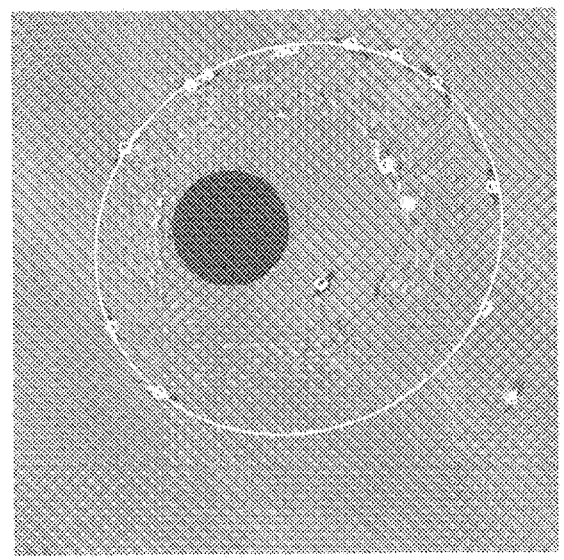
FIG. 10B is an additional example of an image showing lumen detection after removing the guide wire and other noise and model curve fitting using an ellipsoid.

In another embodiment of this invention, 3-D cues are used to refine the strut detection obtained using the 1-D, 2-D and 3-D cues. A 1-D cue can include a point or a scan line. FIG. 10A provides additional details relating to a single ellipsoid model parameter while FIG. 10B illustrates one example of how to refine the stent positions obtained from 2-D cues by the application of 3-D cues. Because the stent is a wire mesh, all struts should lie on an approximately ellipsoidal cylinder. If 2-D ellipsoid cues are used for the strut detection, then these ellipses from multiple neighboring frames should be continuous in 3-D space. Therefore smoothing and averaging the defining parameters of neighboring ellipses can enhance detection accuracy. Each ellipse is defined by a major and minor axis, a center point and a tilt relative to the X-Y plane of the image. One would expect adjacent frames to have substantially similar major and minor axes, center points and tilt.

In FIG. 10A one parameter, the major axis length of the ellipse derived for each frame is plotted (dotted line). Then a 10 frame moving average is calculated for each frame. The resulting set of averages (solid line) then defines the average major axis length for each frame. This process is repeated for the remaining ellipsoid parameters of tilt, center and minor axis. These averaged parameter values for each frame are then used to define the individual ellipses in each frame. Thus, an elliptical shape is fit on a per frame basis as a result of the average values obtained for the tilt, center, minor axis and minor axis for each frame.

Alternatively, in one embodiment, the smoothing can be performed directly onto the 3-D volume formed by stacking ellipses on top of each other. In one embodiment, a 3-D averaging method is used by convolving the 3-D volume with a 3-D blurring kernel. This convolved data set is then evaluated to identify a maximum in the result for each frame.

Figure 11:
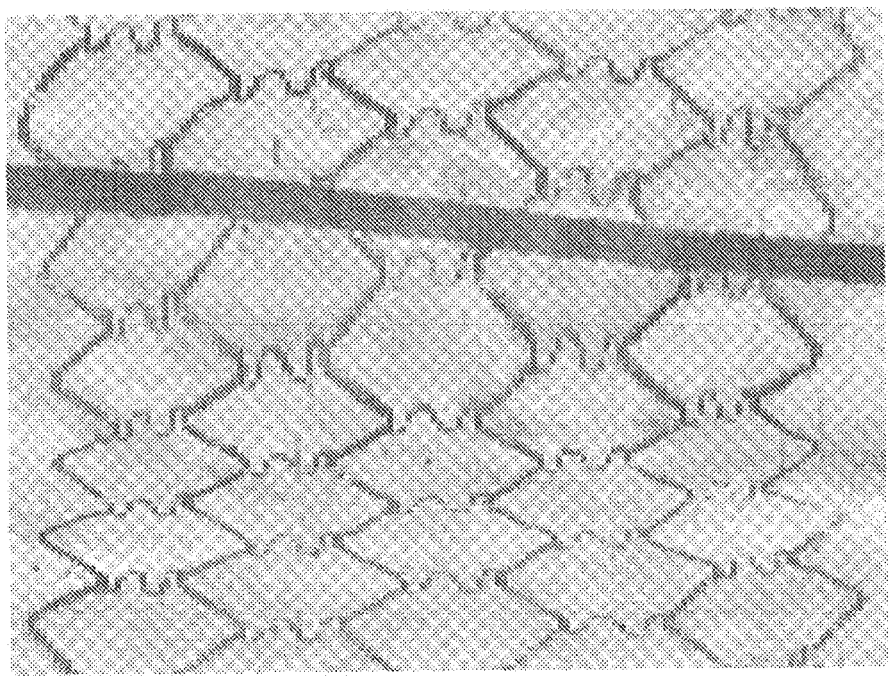
FIG. 11 illustrates an example of an image calculated from the graph in FIG. 4.

FIG. 11 illustrates one example of how to refine strut detection obtained from 1-D cues by 3-D cues. In this figure, the intensity profiles from the graph in FIG. 4 (1-D cues) from each frame are combined to form a 2-D map, where one axis denotes the frame number and the other axis denotes the rotational angle of the catheter. For simplicity, this type of generated 2-D image is called the "cut-open" view of the 3-D image. The images of the struts in the resulting map form continuous lines. Therefore, struts can be detected by direct application of a threshold or a line detector to the image. One such possible line detector is based on the 2-D Hessian matrix.

Figure 12:
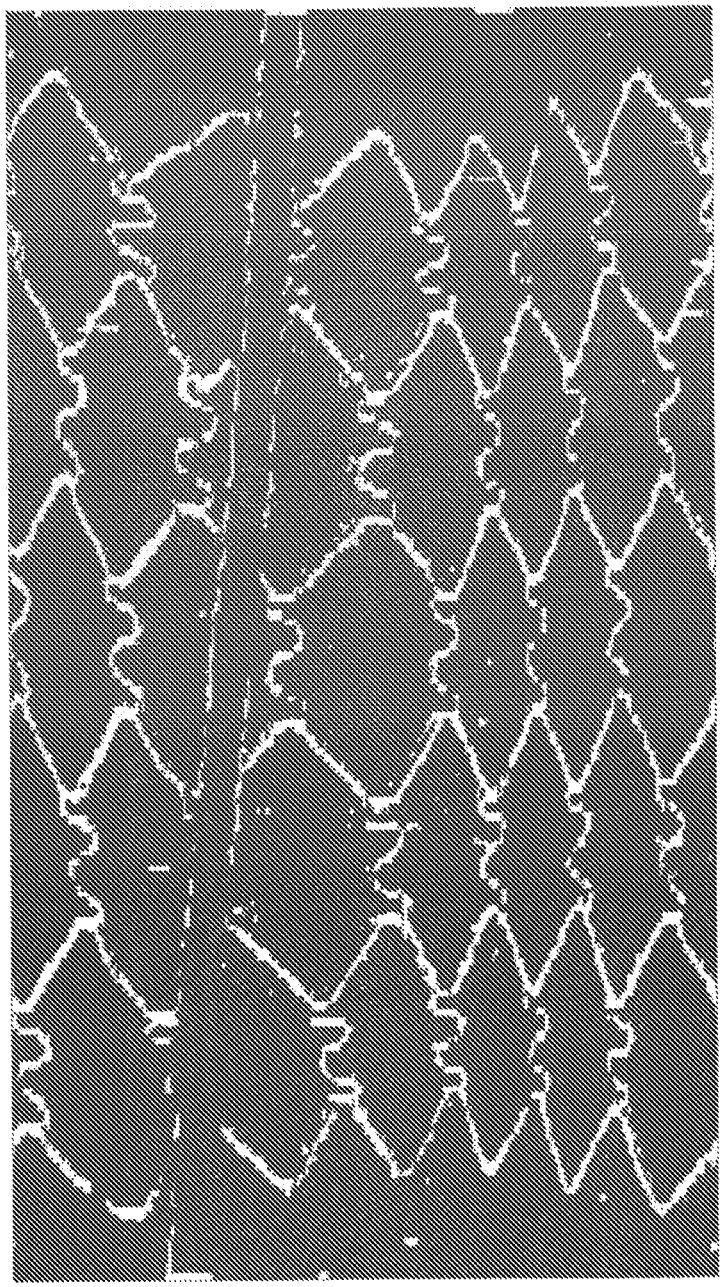
FIG. 12 illustrates the result of applying a line detector to the image in FIG. 11.
Figure 13:
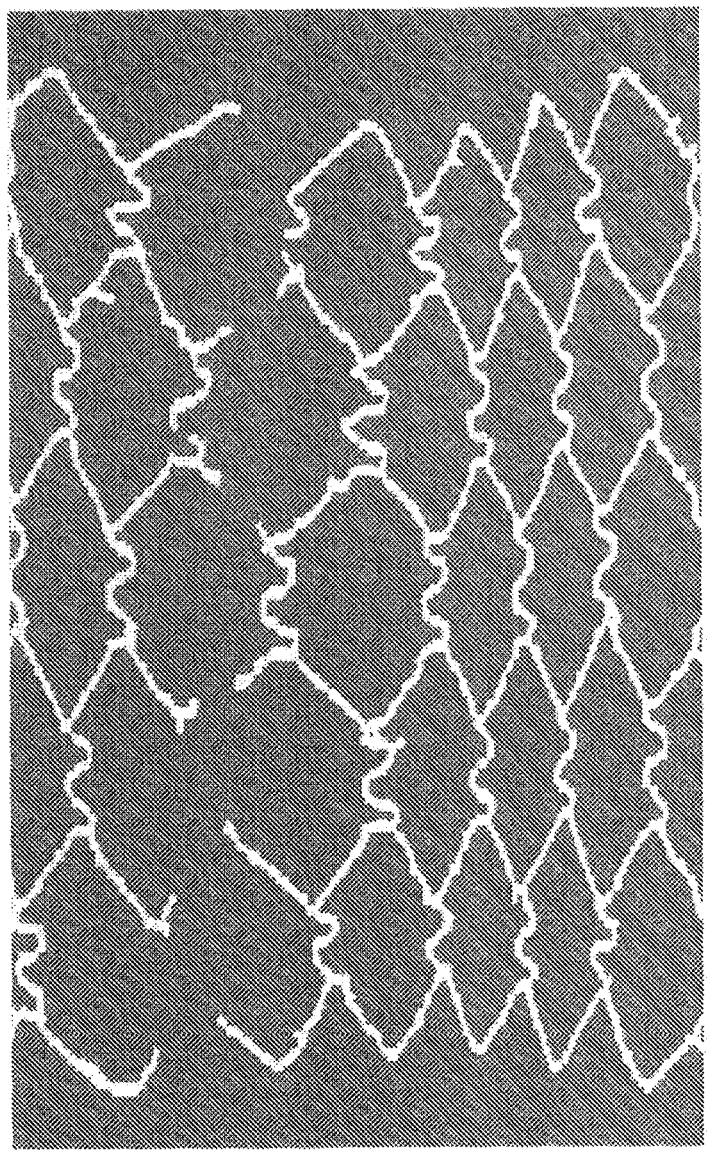
FIG. 13 illustrates an example of refining the result of applying the line detector in FIG. 12.

FIG. 12 shows the line strength calculated by using a ridge detector. Standard morphological image processing methods, such as dilation and erosion, can then be employed to connect adjacent detection points and to remove stray detection points outside of contiguous segments (noise) as is shown in FIG. 13. This is for refining the stent detection methods using inter-frame cues. In 3-D, the stents are continuous wire-meshes. Therefore, in the plan views, the wire meshes are also continuous wire meshes formed by "lines". These lines can be used to refine the struts detection. For example, if a detected "strut" is not on the line formed by struts of neighboring frames, then such "struts" or cues are most likely a false detection.

Another aspect of the invention concerns the measurement and display of the results of the automated stent detection algorithm. The clinically relevant displayed measurements include, among others, the distance from stent to the lumen wall ('stent apposition'), the tissue thickness overlying stent struts ('neointima coverage', or simply 'stent coverage'), and the ratio of the area of the tissue overlying the stent struts to the area enclosed by the stent struts (the 'restenosis ratio').

Figure 14:
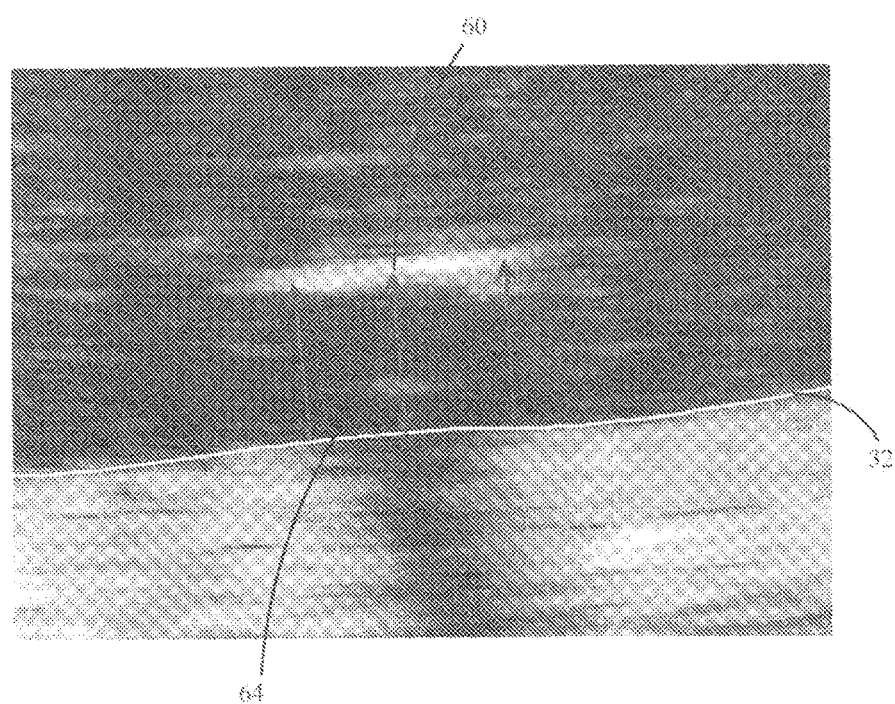
FIG. 14 illustrates an example for the measurement of stent apposition.

FIG. 14 illustrates an image of a measurement used to determine stent apposition. The OCT beam typically can not penetrate metal stent struts, therefore, the OCT image of the stent struts is the top surface 60 of the stent (the first surface upon which the light beam is incident) convolved with OCT system point-spread function. In addition, the struts shadow or prevent reflections from the tissues below the stent. The missing portions for the image of the vessel wall beneath the stent struts are obtained by interpolation of the reflections along the lumen border 32 as previously described.

Figure 15:
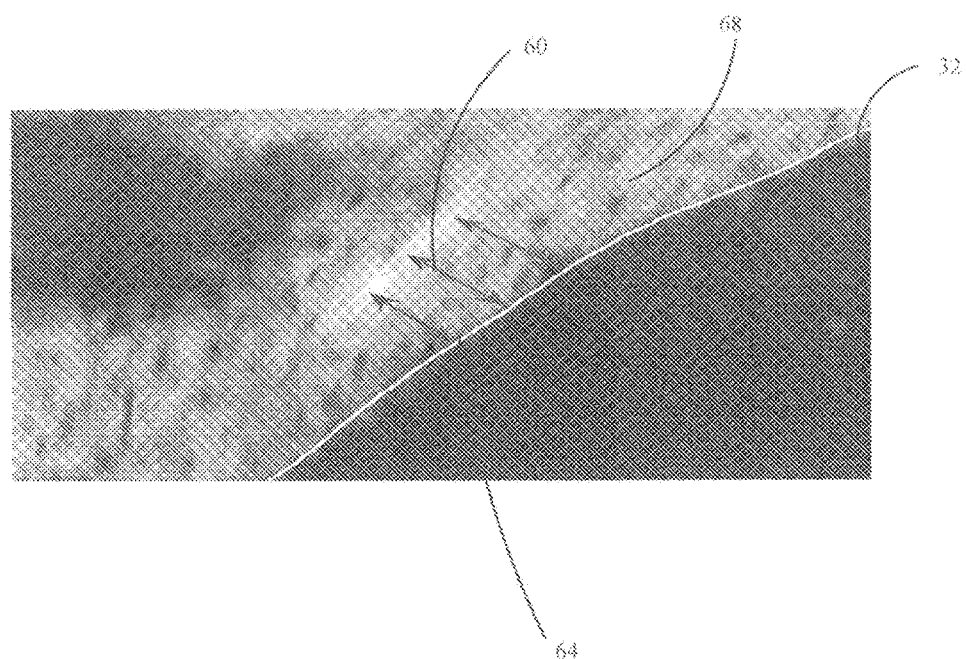
FIG. 15 illustrates an example for the measurement of stent coverage.

Next, the distance 64 from the stent upper surface to the lumen wall is measured from the bright spots to the interpolated curve that represents the vessel wall border. The spots on the stent can be chosen at the middle of the struts, the edges of the struts, or any other combination of points at the front surface of the stents. The apposition distance is obtained by subtracting the thickness of the strut from the distance measured between the front surface reflection and the interpolated vessel border. FIG. 15 depicts the same measurement when the stent is covered by neointima 68.

Figure 16:
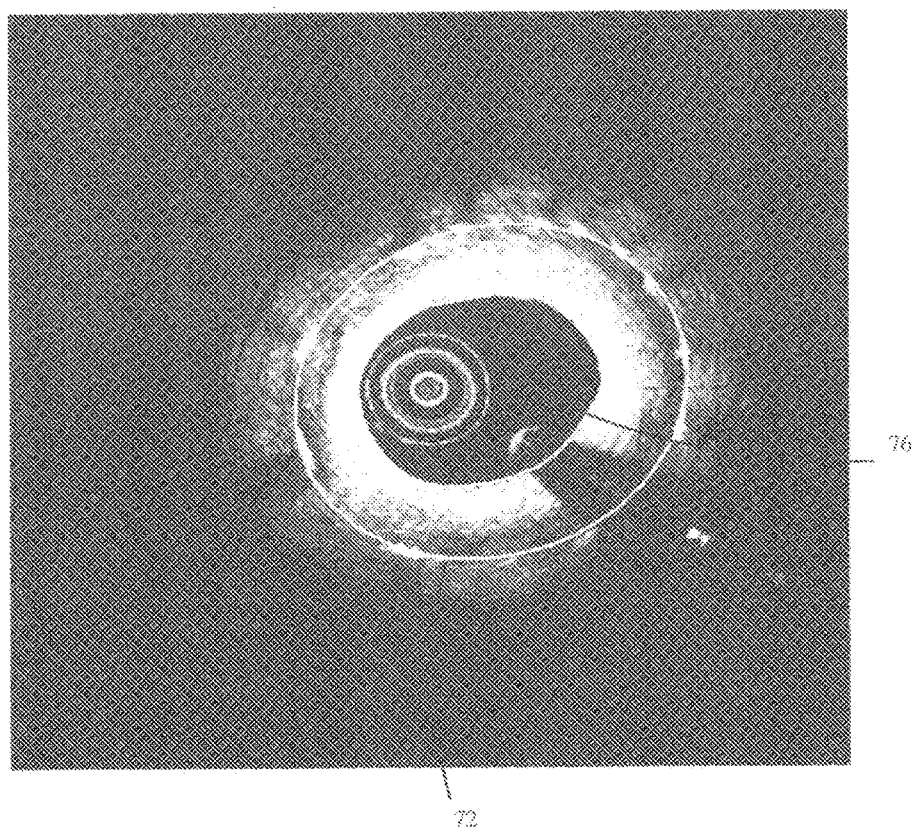
FIG. 16 illustrates an example of measurement of the ratio of area of tissue overlying the stent struts to the area enclosed by the stent struts.

FIG. 16 illustrates the measurement of the ratio of the area of tissue overlying the stent struts to the area enclosed by the stent struts. The stented area is calculated by interpolation of detected struts or by using a model that incorporates the detected stent strut positions (such as a fitted ellipse). In the figure shown, an ellipse 72 formed by the interpolation of the stent struts provides a measure of the surface area enclosed by the stent. A second boundary 76, between the neo intima and the lumen, defines the surface area overlying the stent. From these two area measurements the ratio is calculated. This ratio can be used by clinicians and other system users to evaluate the state of a sample or patient. For example, a stenotic ratio indicative of 50% narrowing or 75% area reduction represents a critical ratio in one embodiment.

Figure 17:
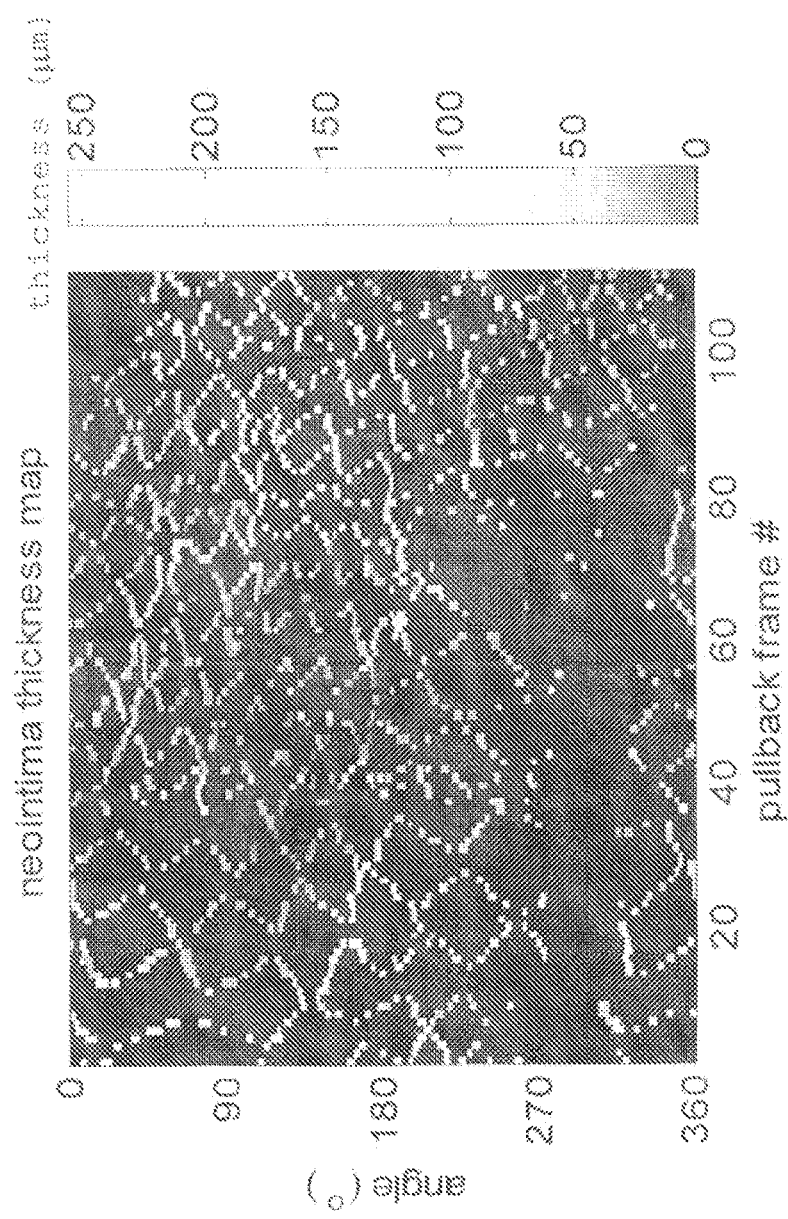
FIG. 17 illustrates an example of displaying the tissue thickness above stent struts.

FIG. 17 illustrates one method for displaying the results of the stent apposition or stent coverage measurements. The positions of the detected stent struts from the entire region of the vessel being viewed are shown as a 2-D map with the X-axis denoting pullback direction or frame direction and the Y-axis denoting the catheter rotational direction. A map is devised to represent the distance from the stent to the lumen wall or the tissue thickness overlying the stent struts, and is used to colorize the detected stent struts in the 2-D map. This display has the advantage of showing several dimensions of information simultaneously (2-D surface stent structure and the corresponding local stent apposition or neointimal thickness values) in an efficient format.

Figure 18A:
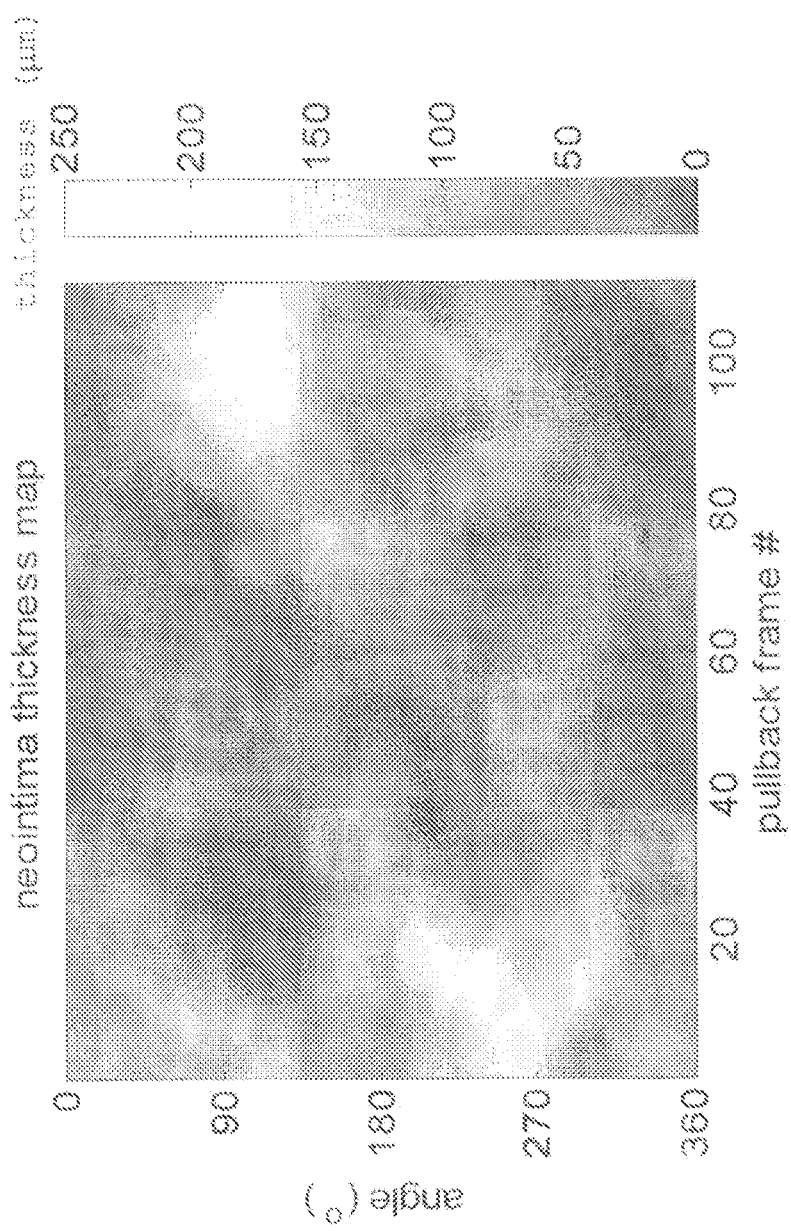
FIGS. 18 (A and B) illustrate another example of displaying the thickness of the tissue above the stent struts.
Figure 18D:
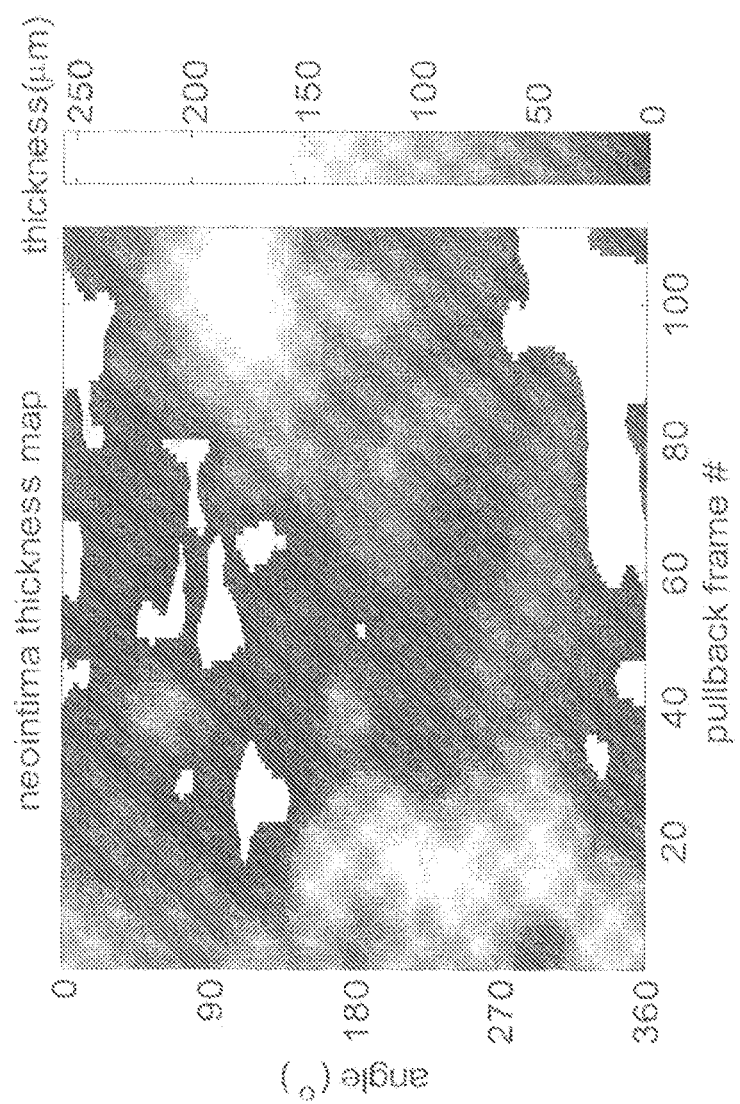

FIG. 18 illustrates an alternative method for displaying the distance from the stent to the lumen wall and tissue thickness overlying the stent struts. In this method, a similar 2-D map is generated without showing the individual stent struts. Rather, the thickness map is averaged and interpolated to cover all regions. Optionally, the display can be enhanced to emphasize potentially clinically adverse regions. One preferred method for enhancing the display is to represent the distance from the stent to the lumen wall above a certain preset threshold (as in the case of stent mal-apposition) or the tissue thickness overlying the stent struts is below a certain preset threshold (as in the case of incomplete stent coverage) by a distinct color.

In the example in FIG. 17, the darker areas (values 20 and below) relative to the lighter areas represent uncovered stent struts on which neointimal thickness is less than the resolution of the OCT imaging system, <about 20 µm. The percentage area of the total surface area below or above this user-defined threshold can also be shown in text in the same display with a different or highlighted color. In addition, to improve the visual appeal of the 2-D maps, a pictorial representation of a generic stent, displayed in a neutral color like black, white, or silver, can be overlaid on the 2-D stent map.

Figure 19:
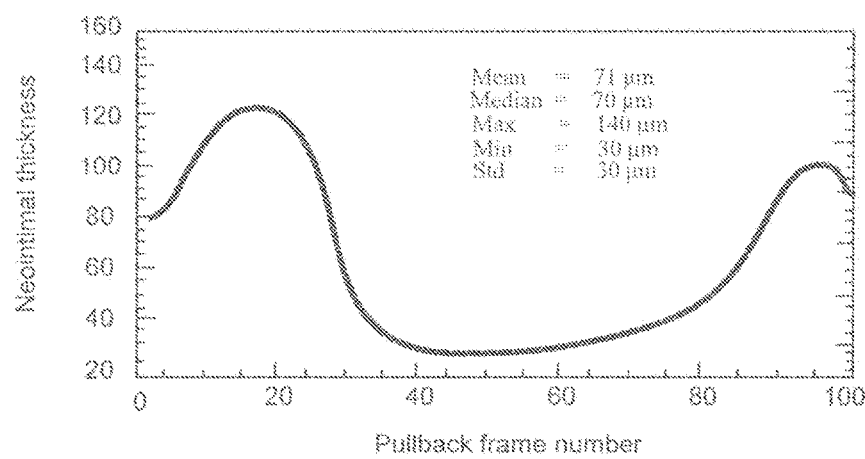
FIG. 19 illustrates an example of a graphical display of the angle-averaged thickness of neointimal coverage on a stent, plotted versus pullback frame number (or, equivalently, pullback distance)

A further alternative for displaying volumetric stent measurements, illustrated in FIG. 19, is to display the stent apposition or stent coverage information into a graph that represents the stent-to-wall distance or neointimal thickness averaged over one revolution of the catheter and plotted against pullback frame number (or pullback distance). This graph, which would typically also include a text summary of the statistical values compiled over the entire stent length, can be shown separately or in combination with one of the 2-D maps.

Figure 20A:
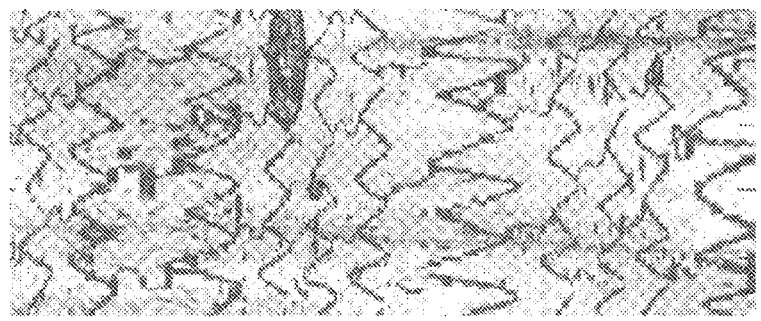
FIGS. 20 (A and B) illustrate an example of correction of an OCT catheter motion artifact due to the beating heart.

Another embodiment of current invention is related to the correction of certain OCT pullback artifacts. One artifact that has special interest in stent strut detection is the motion artifact due to beating of the heart. During each heart beat, the imaging catheter moves relative to the arterial wall. The longitudinal motion of the imaging catheter relative to the arterial wall during a rapid pullback results in the distortion (compression or expansion) of portions of the stent image, as shown in the example in FIG. 20A. This distortion manifests as an error in the correspondence between frame number and actual distance along the length of the stent. Correction of this error can be accomplished is several ways.

Figure 20B:
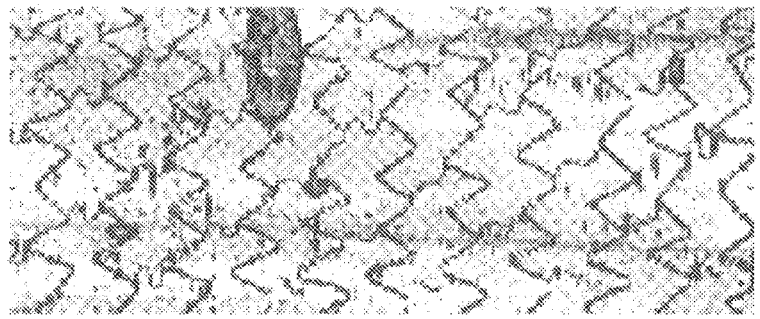

Specifically, once the stent struts have been localized in the OCT image, the periodicity of the images of the transverse stent positions can be evaluated within overlapping segments along the entire length of the stent, by using a windowed Fourier transform, wavelet decomposition, or similar methods for evaluation of spatial frequency distribution. Then a resampling function or distortion correction function can be applied to restore the periodicity of strut images along the length of the stent as shown in FIG. 20B.

Another alternative method uses template matching methods in conjunction with localized expansion or contraction of the stent images to restore the uniformity of the shape of the stent. In addition, another alternative method uses another imaging method such as angiography to determine the actual pullback speed of the OCT imaging sensor to the artery, and thereby resample the image according to this actual pullback speed.

Non-Limiting Software Features and Embodiments for Implementing OCT Methods and Systems With respect to the method described in FIG. 1 and the other embodiments described herein various computer or processor-based systems suitable for interfacing with an OCT probe, such as a catheter probe may be used. Additional details relating to computer-based approaches for implementing stent detection are described below.

The present invention may be embodied in may different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, detecting struts, digital signal processing, detecting valleys or ridges, detecting shadows, detecting lumen boundaries, ellipsoidal modeling, curve and data fitting, OCT images, signal processing, weighting, artifact removal, detecting stents, detecting high reflectivity regions and otherwise detecting or display any of the foregoing and all of the other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, clock signals, region of interest types, formulas, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

What is claimed is:

1. A method of generating a diagnostic representation of a blood vessel and a stent disposed therein, the method comprising:
   storing a set of intravascular measurements in a memory device, the set of intravascular measurements generated in response to an intravascular scan of the blood vessel and the stent disposed therein;
   wherein the set of stored intravascular measurements comprises intravascular data, the intravascular data comprising one or more pullback frames and one or more angles of rotation;
   generating a two dimensional representation of a segment of the blood vessel and the stent disposed therein, wherein the two dimensional representation is oriented relative to a pullback frame axis and an angle of rotation axis; and
   displaying the two dimensional representation of the segment of the blood vessel and the stent disposed therein.

2. The method of claim 1 wherein the stent disposed in the blood vessel is displayed as a plurality of bright narrow features.

3. The method of claim 1 wherein the stent disposed in the blood vessel is displayed as plurality of shadows corresponding to edges of stent struts of the stent.

4. The method of claim 1 further comprising correcting for one or more imaging artifacts.

5. The method of claim 4 wherein one or more of the imaging artifacts is stent distortion.

6. The method of claim 4 wherein one or more of the imaging artifacts is a stent motion artifact.

7. The method of claim 1 further comprising removing noise from image data.

8. The method of claim 1 further comprising enhancing display information to emphasize potentially clinically adverse regions.

9. The method of claim 1 further comprising detecting a plurality of stent struts of the stent disposed in the blood vessel in the set of intravascular measurements.

10. The method of claim 1 wherein the intravascular scan is an optical coherence tomography scan of the blood vessel by which an imaging catheter is pulled back through the blood vessel and the stent.

11. The method of claim 1 wherein the set of intravascular measurements comprises a plurality of scan lines, wherein a scan line corresponds to an angle of rotation of an imaging catheter.

12. The method of claim 1 further comprising displaying an indicia overlaid on one or more stent struts of the displayed representation.

13. The method of claim 12 wherein the indicia is indicative of malapposition.

14. The method of claim 9 wherein detecting a plurality of stent struts of the stent disposed in the blood vessel comprises
   identifying at least one stent strut of the stent by detecting a one-dimensional local cue in one or more scan lines of the optical coherence tomography image data set and
   displaying the representation of the blood vessel and one or more identified stent struts identified using the one or more one-dimensional local cues.

15. A system for generating a diagnostic representation of a blood vessel and a stent disposed therein, the system comprising:
   an optical coherence tomography system comprising an input for probe data, the optical coherence tomography system comprising:
   an electronic memory device comprising instructions; and
   an electronic processor in communication with the electronic memory device, the electronic processor operable to execute the instructions to perform operations comprising:
   store a set of intravascular measurements in a memory device, the set of intravascular measurements generated in response to an intravascular scan of the blood vessel and the stent disposed therein;
   wherein the set of stored intravascular measurements comprises intravascular data, the intravascular data comprising one or more pullback frames and one or more angles of rotation;
   generate a two dimensional representation of a segment of the blood vessel and the stent disposed therein, wherein the two dimensional representation is oriented relative to a pullback frame axis and an angle of rotation axis; and
   display the two dimensional representation of the segment of the blood vessel and the stent disposed therein.

16. The system of claim 15 wherein the instructions further cause the processor to correct for one or more imaging artifact.

17. The system of claim 15 wherein the instructions further cause the processor to remove noise from image data.

18. The system of claim 15 wherein the instructions further cause the processor to enhance display information to emphasize potentially clinically adverse regions.

19. The system of claim 15 wherein the instructions further cause the processor to display an indicia overlaid on one or more stent struts of the displayed representation.

20. The system of claim 15 wherein the instructions further cause the processor to detect a plurality of stent struts of the stent disposed in the blood vessel in the set of intravascular measurements.

21. The system of claim 20 wherein the instructions further cause he processor to
   identify at least one stent strut of the stent by detecting a one-dimensional local cue in one or more scan lines of the optical coherence tomography image data set and
   display the representation of the blood vessel and one or more identified stent struts identified using the one or more one-dimensional local cues.

* * * * *